United States Patent [19]

Chang et al.

[11] Patent Number: 4,820,416
[45] Date of Patent: Apr. 11, 1989

[54] REMOVAL OF BILIRUBIN BY THE PSEUDOPEROXIDASE ACTIVITY OF IMMOBILIZED HEMOGLOBIN

[75] Inventors: Thomas M. S. Chang, St-Lambert; Joseph N. Daka, Montreal, both of Canada

[73] Assignee: The Royal Institution for the Advancement for Learning (McGill University), Montreal, Quebec, Canada

[21] Appl. No.: 95,413

[22] Filed: Sep. 10, 1987

[51] Int. Cl.[4] .................... B01D 15/00; B01D 43/00
[52] U.S. Cl. ................................. 210/632; 210/759; 210/763; 435/25; 435/28; 435/264; 435/269; 436/97; 436/178
[58] Field of Search ............... 210/632, 758, 759, 763; 436/97, 178; 435/25, 28, 264, 269

[56] References Cited

U.S. PATENT DOCUMENTS 4,563,429 1/1986 Doumas et al. .................... 436/97

OTHER PUBLICATIONS

Hawley, G., The Condensed Chemical Dictionary, Eighth Edition, 1971, pp. 455–456.
Chang, T. M. S., Semipermeable Microcapsules, (1964), Science, vol. 146; 524–525.
Chang, T. M. S., Artificial Cells Containing Multienzyme Systems, (1985), Meth. Enzymol., 112, 195–203.
Chang, T. M. S., Applications of Artificial Cells in Medicine and Biotechnology, (1987), Biomat. Art. Cells Org., 15(1), 1–20.
Sideman S. et al., Preparation of a Biocompatible Albumin-Coated Iron Exchange Resin for Bilirubin Removal from the Blood of Jaundiced Newborns, (1983), J. Biomed. Mat. Res., 17, 91–107.
Keipert P. et al., Cross-Linked Stroma-Free Polyhemoglobin as a Potential Blood Substitute, Int. J. Artif. Org., vol. 5, 383–385, (1982).
Sung C. et al., An Immobilized Enzyme Reactor for the Detroxification of Bilirubin, (1986), Biotech. and Bioeng., vol. 27, 1531–1539.
Keipert P. et al., Preparation and in vitro Characteristics of a Blood Substitute Based on Pyridoxylated Polyhemoglobin, (1984), Appl. Biochem. and Biotech., vol. 10, 133–141.

Primary Examiner—W. Gary Jones
Attorney, Agent, or Firm—Margaret M. Duncan

[57] ABSTRACT

The present invention relates to a process for oxidizing bilirubin which comprises reacting a solution containing bilirubin with hemoglobin, either in free or immobilized form, in the presence of an oxidizing agent such as hydrogen peroxide. This process if useful in reducing bilirubin levels in the blood of severely jaundiced patients. It also provides a basis for determining bilirubin levels in a fluid.

14 Claims, 5 Drawing Sheets

REMOVAL OF BILIRUBIN BY THE PSEUDOPEROXIDASE ACTIVITY OF IMMOBILIZED HEMOGLOBIN

BACKGROUND OF THE INVENTION

Bilirubin, a water-insoluble tetrapyrrole, is an orange-yellow pigment produced from the heme. It can poison many vital cell functions of the human body but the liver clears it from the blood by conjugating it to a water-soluble form and excretes it into the bile. However, some newborns, due to their incomplete maturation of the several steps involved in the bilirubin metabolism and excretion, have bilirubin concentrations in their blood which are much greater than the normal upper limits, thereby leading to jaundice in severe cases. Severely jaundiced babies can suffer from mental retardation, deafness, seizures and death. In children and adults, disorders of the liver can also lead to the accumulation of bilirubin to toxic levels in the body.

These concerns are the basis for research into finding suitable controls for bilirubin toxicity. So far, there are two commonly used approaches for severely jaundiced patients: phototherapy and exchange transfusion. However, both techniques present severe drawbacks and limitations.

Phototherapy is inadequate for the treatment of severe cases of jaundice since only 15% of the total bilirubin can be photoisomerized through the skin. Furthermore, phototherapy induces DNA damage and causes depletion of riboflavin, tryptophan and histidine in cultured mammalian cells.

In severe cases of jaundice, patients can undergo blood exchange transfusion. However, the mortality of a single exchange transfusion approaches 1% and some patients must undergo more than one exchange. Problems such as hypoglycemia, acidosis, coagulopathies as well as chances of transmitting viral infections such as hepatitis and AIDS to the patients are also common risks inherent to this approach.

In order to avoid problems associated with exchange transfusions, various efforts have been made to develop resins for removal of bilirubin from the blood by adsorption through chromatography. Generally, the selectivity of this technique is poor and consequently several other blood components including essential compounds such as thyroxine, cortisol and aldosterone are also removed from the blood stream.

Recently, bilirubin oxidase has been suggested as a treatment approach. However, this enzyme is expensive and not readily available.

Therefore, an inexpensive, easily accessible method for the removal of bilirubin from blood would be highly desirable.

SUMMARY OF THE INVENTION

In accordance with the present invention, there is provided a process for oxidizing bilirubin which comprises reacting a solution containing bilirubin with hemoglobin in the presence of an oxidizing agent. Hemoglobin can be used either in free form or immobilized. Immobilization includes microencapsulation, matrix entrapment, covalent linkage to carriers, cross linked into polyhemoglobin, etc. In the case where hemoglobin is immobilized, glucose oxidase may be included. In this case, the oxidation reaction takes place in the presence of glucose which is normally available in the blood stream and the presence of other oxidizing agents becomes unnecessary.

In cases where bilirubin is conjugated to large proteins such as albumin, oxidation can be accomplished by using hemoglobin either in free form, adsorbed or bound on a suitable surface. Polyhemoglobin or cross-linked hemoglobins can also be used as oxidation catalysts in this case. The particulars of the present invention will be more readily understood by referring to the following description.

DETAILED DESCRIPTION OF THE INVENTION

The present invention relates to a process for oxidizing bilirubin by the use of hemoglobin either in free form or immobilized in the presence of hydrogen peroxide, or by the use of immobilized hemoglobin and glucose oxidase in the presence of glucose. It is to be noted that bilirubin is oxidized by the oxidizing agent and that hemoblobin acts as a catalyst in the reaction. Although various oxidizing agents such as alkyl and aryl peroxides can be used in the context of the present invention, hydrogen peroxide is preferred.

(a) Oxidation of bilirubin using hemoglobin in free form

When it is desired to oxidize bilirubin in the presence of free hemoglobin and hydrogen peroxide or any equivalent thereof, 0.001 g to 0.025 g of hemoglobin may be dissolved in 5.0 ml of a saline solution and reacted with a bilirubin solution containing 0.0001% to 0.05% of hydrogen peroxide and having a bilirubin concentration varying between 1.0 mg/l and 200 mg/l. It is to be noted that the optimal hydrogen peroxide concentration should be such as to avoid unnecessary reactions with other blood components. Upon oxidation, the colour of bilirubin changes from bright yellow to very light, almost colourless green. Therefore, bilirubin oxidation can be monitored by following the disappearance of an absorbance band at 440 nm on a Cary 219 double beam UV-VIS spectrophotometer.

(b) Oxidation of bilirubin using hemoglobin immobilized within semipermeable microcapsules Once the hemoglobin molecules have been inserted in the desired semipermeable membrane designed in such a manner that only bilirubin hydrogen peroxide and their by-products are allowed to penetrate and to leave the cell, these microcapsules may be used for oxidation of bilirubin in the presence of a suitable oxidizing agent.

The semipermeable microcapsules may be prepared by using the following general procedure. The molecule to be encapsulated is first emulsified in an organic solution to which a suitable material is added in order to form a permanent membrane at the interface of each microdroplet of the emulsion either by interfacial coacervation or by interfacial polycondensation. The microcapsules that are formed are then transfered to an aqueous medium, for example, by centrifugation and resuspension in an appropriate series of fluids. In the case of coacervation, these fluids may be n-butylbenzoate containing Span 85 followed by Tween 20 detergent solution and then by water; in the polycondensation procedure, n-butylbenzoate is omitted.

The size of the microcapsules is determined in the first step mainly by the speed of the mechanical emulsifier and the concentration of emulsifying agent. The thickness of the membrane is determined mainly by the concentration of the materials used to form it. The coacervation technique can be used to form membranes from polymers other than collodion that are soluble inorganic solvents, for example polystyrene, cellulose acetate, etc. The polycondensation technique can be used with diamines other than hexanediamines or with polyamines. Further details concerning the preparation of the microcapsules to be used in the context of the present invention as well as protein encapsulation techniques are described in (1964) Science, vol. 146; 524–525, (1985) Meth. Enzymol. 112, 195–203 and Biomat. Art. Cells Org., 15(1) 1–20 (1987).

Once the microcapsules are formed, bilirubin can be oxidized by hemoglobin molecules immobilized in the microcapsules in a buffer solution in the presence of an oxidizing agent such as hydrogen peroxide. Up to 90 % of concentrations of bilirubin ranging from 1.0 mg/l to 200 mg/l can be oxidized by using hemoglobin concentrations varying between 0.05 mg/l to 500 mg/l. Again, bilirubin conversion may be monitored by assessing the disappearance of an absorbance band at 440 nm on a double beam UV-VIS spectrophotometer.

The present invention will be more readily understood by referring to the following examples which are provided in order to illustrate rather than limit the scope of the present invention.

EXAMPLE 1

Oxidation of bilirubin using hemoglobin in free form

Figure 1:
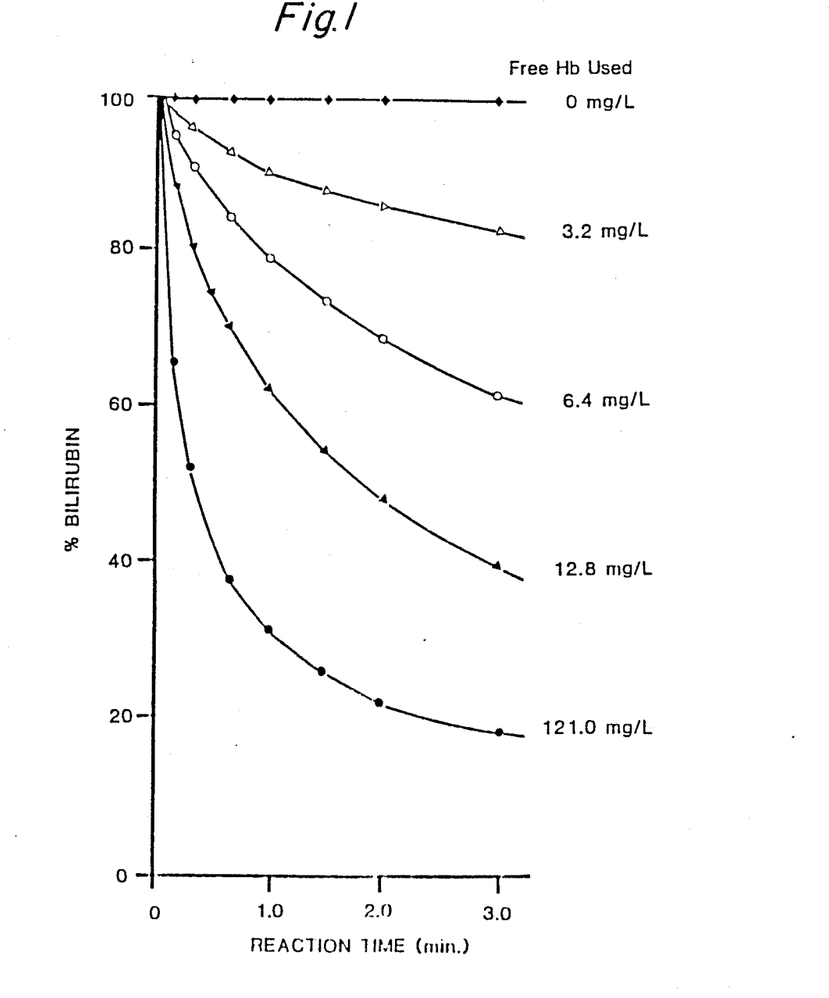
FIG. 1 represents the effect of various free hemoglobin concentrations on the oxidation ratio of bilirubin.
Figure 2:
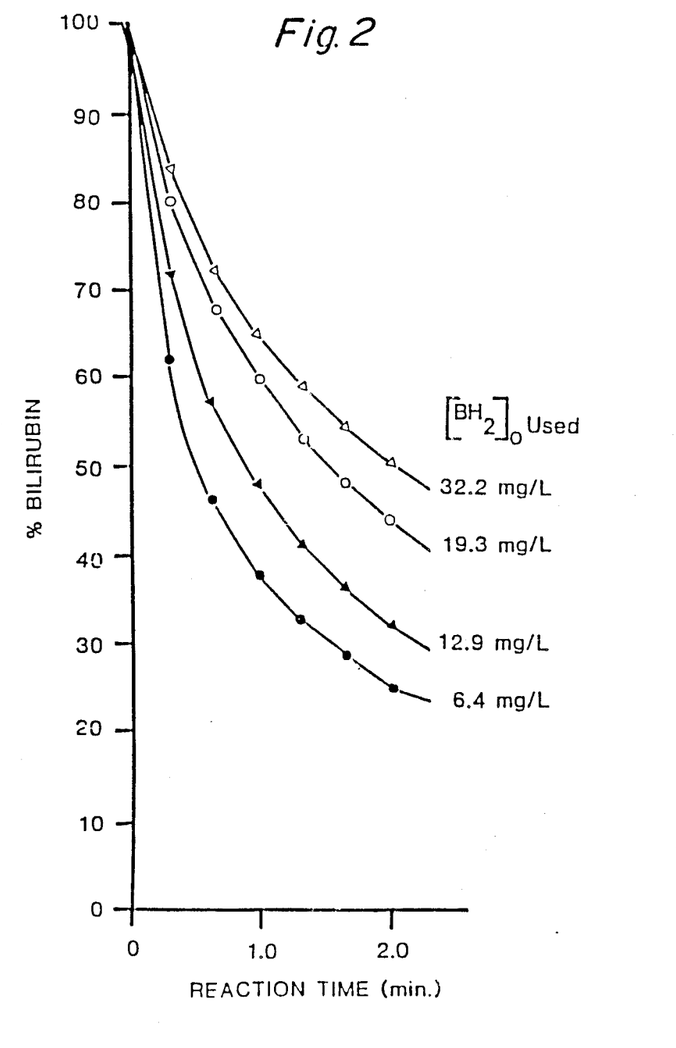
FIG. 2 represents the effect of increasing bilirubin concentrations on the oxidation ratio of bilirubin using a fixed free hemoglobin concentration.

Analyses were conducted in 3.0 ml of buffer (pH 7.0) in a cuvette with hydrogen peroxide concentration fixed at 0.03% or 9.8 mM. Two sets of experiments were conducted: one in which hemoglobin concentration was varied and one in which bilirubin concentrations were varied. In a first set of experiments, crystallized, dialyzed and lyophilized type I stroma-free hemoglobin obtained from bovine blood and purchased from Sigma Chemical Company was diluted in a saline solution in order to obtain a stock concentration of 2 g/l from which a series of dilutions were made in order to obtain the desired concentrations. Bilirubin obtained from bovine gall stones was mixed with 0.1M $Na_2CO_3$ in order to obtain a stock solution of 2 g/l. Exposure of the bilirubin solution to light was avoided by covering the containers with aluminum foil. Hemoglobin concentrations were varied between 3 and 122.0 mg/l in the first set of experiments while bilirubin was fixed at 33.3 mg/l. In the second set of experiments, bilirubin concentrations were varied between 6.0 and 42.0 mg/l while hemoglobin concentration was maintained at 33.3 mg/l. As it can be seen in FIGS. 1 and 2, a strong oxidation rate is first observed followed by slower reaction rates as time progresses. It is to be noted that while the percent conversions of bilirubin increases with increasing amounts of hemoglobin in solution, this percentage decreases as bilirubin concentrations are increased.

EXAMPLE 2

Bilirubin oxidation using hemoglobin immobilized in semipermeable microcapsules

Microcapsules containing immobilized hemoglobin were prepared by adding 9 ml of a 14.6 g/dl hemoglobin solution to 105 ml of water-saturated ether. Crystallized, dialyzed and lyophilized type 1 stroma-free hemoglobin obtained from bovine blood was also used. The resulting solution was immediately mixed at 1200 r.p.m. using a magnetic stirrer. After 5 seconds, 120 ml of 4 g/dl collodion (4 g of cellulose nitrate in 17.5 ml alcohol and 82.5 ml ether) was poured into the emulsion and stirred vigorously for 60 seconds. The solution was then allowed to stand undisturbed for 45 minutes in order to allow the formed artificial cells to completely sediment. Most of the supernatant was discarded and immediately 30 ml of n-butylbenzoate containing 60 ul Span-85 was added. Stirring was repeated at 1200 r.p.m. for 30 minutes. This benzoate/span treatment is necessary in order to make the cell membranes flexible. The contents of the beaker were then allowed to stand unstirred and uncovered for 30 minutes. The final step was to transfer the artificial cells containing hemoglobin from the mother organic liquid to the aqueous medium. This was accomplished by centrifugation at 350 r.p.m. for 60 seconds, followed by replacement of the supernatant with 25 ml of 50% Tween-20 solution. After mixing the suspension at 1200 r.p.m. for 30 seconds, 25 ml of distilled water was added. In order to separate this slightly turbid supernatant, from the cell suspension, another centrifugation at 350 r.p.m. was performed for 60 seconds. Finally, the resultant cells were washed six times with 1% Tween-20 solution until no apparent traces of n-butylbenzoate could be detected. The hemoglobin cells thus prepared were stored and suspended in saline at 4° C. All the previous steps were carried out at 4° C. The microcapsules are then ready to be used. The exact amount of hemoglobin contained in the microcapsules can be assayed by using the method described in (1967) Brit. J. Haemat. 13, (suppl.) 71–75.

Oxidation reactions of bilirubin obtained from bovine gall stones and mixed with a solution of 0.1 M $Na_2CO_3$ were performed in 8 ml of a stirred buffer solution (pH 7.0). The concentration of $H_2O_2$ was fixed at 0.03% or 9.8 mM. While the microcapsules concentration was fixed at 6.25%, bilirubin concentrations varied between 6.0 and 42.0 mg/l in a first set of experiments. In a second set of experiments, the concentration of $H_2O_2$ was maintained to previously mentioned levels while bilirubin concentration was fixed to 10.0 mg/l and hemoglobin microcapsules were varied in order to obtain a concentration varying between 0 and 46.8 mg/l of hemoglobin.

Figure 3:
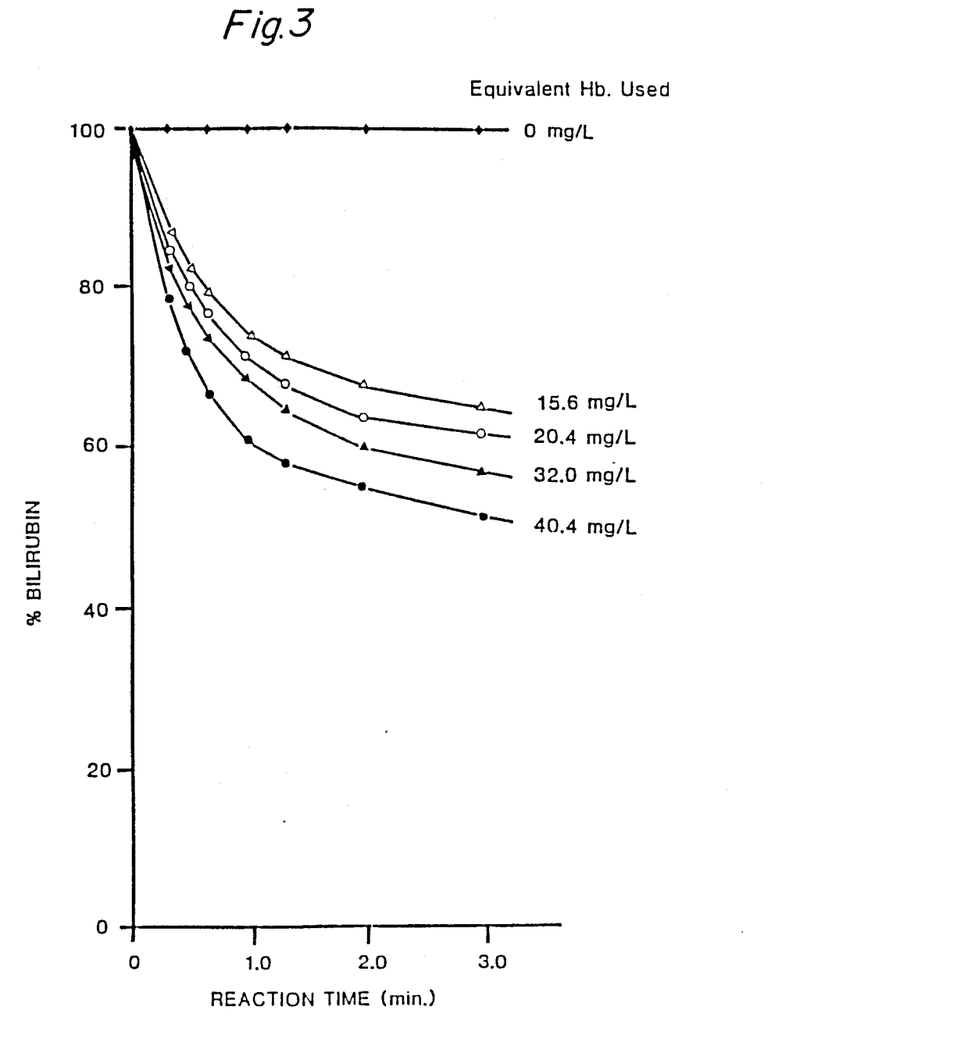
FIG. 3 represents the effect of various microencapsulated hemoglobin concentrations on the oxidation ratio of bilirubin.
Figure 4:
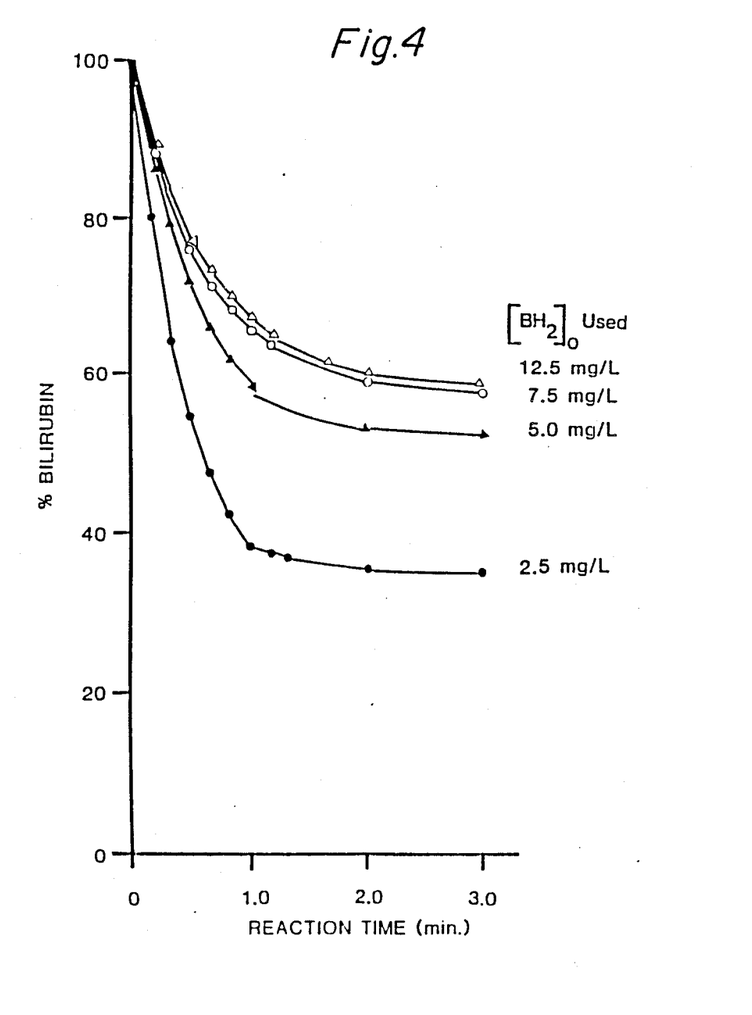
FIG. 4 represents the effect of increasing bilirubin concentrations on the oxidation ratio of bilirubin using a fixed microencapsulated hemoglobin concentration.

FIGS. 3 and 4 demonstrate that the percent conversion of bilirubin is somewhat lower when hemoglobin is encapsulated. However, reaction rates can be easily compared to the rates obtained in Example 1.

EXAMPLE 3

Bilirubin oxidation using intermolecular cross-linked stroma-free hemoglobin

Preparation of the catalyst was done at 4° C. Detailed procedure has already been published (Intern. J. Artif. Org., Vol. 5, 1982, pp. 383-385). To 4 ml of 1.3M lysine monohydrochloride in 0.1M phosphate buffer, 300 ml of stroma-free hemoglobin (10 g/dl) was added. Later, 30 ml of 0.25M glutaraldehyde in 0.1M phosphate buffer was added slowly. The resulting solution was left stirring at 10° C. Cross-linked polyhemoglobins formed within one hour. These were then washed several times with saline to remove the unbound glutaraldehyde.

In the experiments, 0.5 ml of the crosslinked hemoglobin was added to a total reaction mixture of 8.0 ml, containing bilirubin (5 mg/l–40 mg/l) and hydrogen peroxide (0.03%). Progress of the reaction was monitored as before. The system showed effectiveness as for the microcapsules discussed above.

EXAMPLE 4

Bilirubin oxidation using covalently immobilized hemoglobin 5 g of nylon granules were dissolved in 10 ml of concentrated hydrochloric acid under vigorous stirring. After dissolution, the mixture was quickly poured in 500 ml of ice cold distilled water. The formed nylon fibres were washed in methylene chloride and then distilled water. They were then transferred to a buffer solution containing 0.25M glutaraldehyde, pH 9.5. After 1 hour, the resultant activated supports were allowed to react with 5 ml of hemoglobin solution (2.0 g/l) at 4° C. overnight. The following day, excess hemoglobin was washed away with several volumes of saline and phosphate buffer (pH 7.4) mixtures.

The activity of these systems were tested by passing solutions of bilirubin (5.0 mg/l–40 mg/l) and hydrogen peroxide (0.03%) through a 5 ml column of the catalyst. The peristaltic pump was used to circulate the solution. The progress of the reaction was monitored at 440 nm as already discussed. Although slower than the other immobilized forms, 90% of the bilirubin was removed or oxidized within an hour.

When not in use, the fibres were stored in saline at 4° C.

EXAMPLE 5

Bilirubin oxidation using microcapsules containing glucose oxidase

Collodion microcapsules were prepared as outlined earlier, except that the hemoglobin (14.6 g/dl) contained 0.1 g of glucose oxidase (20,000 U/g) from Sigma. It is to be noted that the concentration of glucose oxidase may vary from 1 to 30% by weight of bilirubin to be oxidized. Nylon cells were made according to the previously published procedure (J. Molecular Catalysis, s 1981, Vol. 11, 89-90). Instead of alcohol dehydrogenase and malic dehydrogenase, we used a mixture (2.5 ml) of hemoglobin and glucose oxidase. The same quantity of enzyme was used. Prepared cells were stored at 4° C. in saline, when not in use.

Oxidation reactions were done as for the collodion cases, but did not contain externally added $H_2O_2$. The oxidizing agent was generated insitu after adding 0.5 ml of glucose (10 g/l) to an 8 ml solution containing bilirubin and microcapsules. Complete oxidation of bilirubin was observed within an hour.

Thus various forms of immobilized hemoglobin are effective in removing bilirubin in the presence of hydrogen peroxide.

EXAMPLE 6

Influence of pH variations on bilirubin conversion

Figure 5:
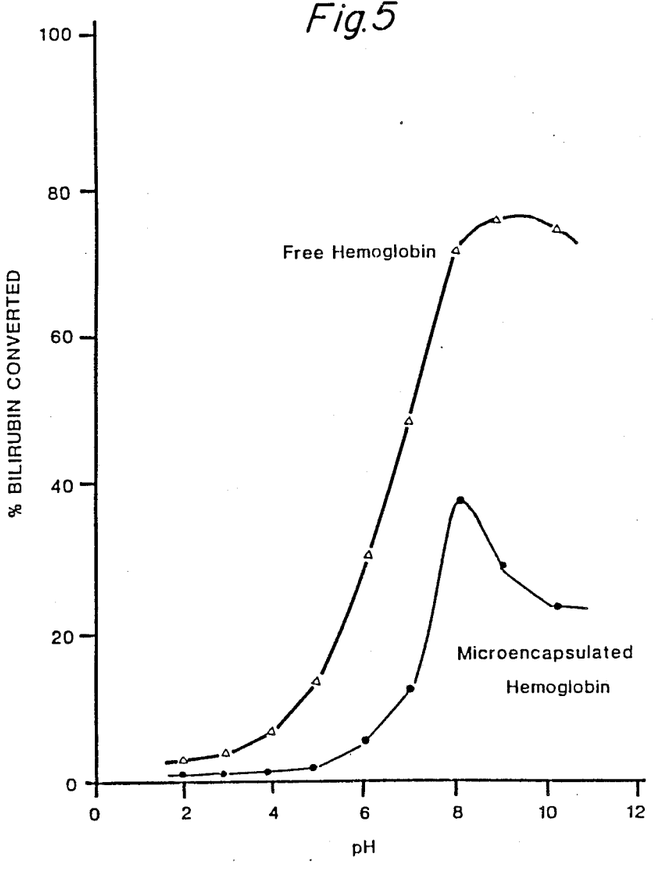
FIG. 5 represents the influence of pH on bilirubin oxidation for both free and microencapsulated hemoglobin.

The pH of the solution in which bilirubin is oxidized by hemoglobin catalysis represents a critical variable in the reaction. Thus, an independent series of tests were conducted following the procedures described in Examples 1 and 2 but using respectively bilirubin and hydrogen peroxide concentrations of 25.0 mg/l and 4.0 mM while the concentrations of free and immobilized hemoglobin (microcapsules) were respectively fixed at 74.1 mg/l and 6.26% v/v. Results, which are exemplified in FIG. 5, show that the maximum percent conversions with free hemoglobin occured at 8.9 while the optimum pH value for microcapsules was found to be 8.0.

Kinetic Model for bilirubin oxidation using hemoglobin as a catalyst

The mechanism by which hemoglobin catalyzes the oxidation of bilirubin by hydrogen peroxide is still to be determined. It is most probable that it follows the widely accepted scheme for peroxidases:

$$E + H_2O_2 \rightarrow I \tag{i}$$

$$I + BH_2 \rightarrow II + BH^o \tag{ii}$$

$$II + BH_2 \rightarrow E + BH^o \tag{iii}$$

$$2BH^o \rightarrow BH_2 + B_o \tag{iv}$$

Where I and II are modified but active enzyme intermediates; $BH_2$ and $B_o$ are the native and oxidized forms of bilirubin, respectively. The $BH^o$ is the free radical intermediate of bilirubin and E is the enzyme. In the present situation, this E stands for hemoglobin, Hb.

Detailed analysis of the above mechanism leads to a complicated rate expression with too many kinetic constants, which can be cumbersome for general application. In order to simplify the analysis, it was assumed that in the presence of excess or fixed amount of hydrogen peroxide, the following Michaelis-Menten rate equation can be used to represent the kinetics of the bilirubin breakdown:

$$v = k[Hb][BH_2]/(K_m + [BH_2]) \tag{1}$$

Where $k$ and $K_m$ respectively stand for the true rate constant and the Michaelis enzyme constant.

When a biocatalyst such as hemoglobin is enclosed in a semipermeable membrane such that only bilirubin, hydrogen peroxide and their products are allowed to enter and leave the cell, a very complicated kinetic situation arises. The complexity can be due to a number of factors often difficult to measure separately. These factors may include:

(a) The conformation of the proteinaceous biocatalyst may change due to the microencapsulation and hence may alter its activity.

(b) The size, shape and chemical struture of the pores through the cell may affect the substrates' accessability to the catalyst.

(c) The heterogeneous reaction may be diffusion-controlled.

Since the exact extent to which each of these factors influences the reaction is uncertain, it would be difficult to derive a single, simple rate equation that will satisfactorily reflect the contribution of each of these factors. However, it is believed that the observed kinetics with the microencapsulated hemoglobin is merely a modification of the reaction behaviour found with the free hemoglobin. In this respect, a modifying factor is introduced into equation 1, and thus the following working expression for the immobilized biocatalyst is derived:

$$R = vw = k'[Hb][BH2]/(K_m + [BH2]) \quad (2)$$

Wherein R is the observed reaction rate, k' is the modified or pseudo rate constant equal to k.w. This constant can be influenced by membrane porosity, mass transfer, cell size and many other factors. Consequently a change in some effects may result in the altered kinetics of the hemoglobin.

In this study, the reaction was monitored by following the decrease in the absorbance readings due to bilirubin disappearance. Thus R could be written in a differential form as:

$$R = -d[BH2]/dt \quad (3)$$

With this expression, equation 2, was integrated subject to the boundary conditions that:
(i) at time=0, $[BH2] = [BH2]_o$ and
(ii) at time=f, $[BH2] = [BH2]_f$.

The final result of this integration was the following:

$$\ln x = a - bt \quad (4)$$

where $$x = [BH2]_f/[BH2]_o \quad (5)$$

$$a = ([BH2]_o - [BH2]_f)/K_m \quad (6)$$

$$b = V'_m/K_m = wk[Hb]/K_m \quad (7)$$

According to equation 4, one can directly obtain estimates of b or $V'_m/K_m$ ratios from the slopes of the ln x versus time plots. Evaluation of individual values of $v'_m$ and $K_m$ can be made with the aid of the values of the intercepts (i.e.; values of a), but for quick analysis of the $V'_m/K_m$ ratios, equation 4 provides a simpler and cheaper route than the Lineweaver-Burk approach which requires the use of many reaction rates and many substrate concentrations before similar kinetic parameters can be calculated.

Fundamentally the results obtained in the context of the present invention are consistent with the predictions of the kinetic model represented by equation 4. At time periods less than 1 minute, the amount of $[BH2]f$ formed is still too small to have any significant effect. However when bilirubin is increased within this time, frame $[BH2]o$ goes up and reduces the percent conversions as it can be seen in FIGS. 2 and 4. On the other hand, when the initial bilirubin concentration (i.e.; $[BH2]o$) is fixed and hemoglobin varied, $[BH2]f$ in equation 6 grows at a fairly faster rate and at the expense of $[BH2]o$. Also, since b increases with Hb, one would expect a faster drop of bilirubin from 100%. This faster drop may be visualized in FIGS. 1 and 3. At infinite times, the effect of bt on percent conversion becomes negligible compared to $[BH2]f$ and the reaction tends to be independent of the time effect.

Furthermore, in order to provide estimates of the kinetic parameters, the Lineweaver-Burk plots were used to calculate values of Km and Vmax. For this purpose, the concentration of free hemoglobin was fixed at 32 mg/l and the concentration of the microencapsulated biocatalyst was fixed at 6.25% v/v or 23.3 mg/l. The results are given in Table III. It is to be noted that the Km values for the free and immobilized hemoglobin are fairly comparable, suggesting that the collodion membrane around the cells does not impose a significant limitation to the passage of the substrates. Also, the fact that these Km values are smaller than those found with bilirubin oxidase tends to lead toward the conclusion that hemoglobin is a better biocatalyst for bilirubin oxidation than bilirubin oxidase. Furthermore, when compared to bilirubin oxidase, cheaper prices for hemoglobin provide an even more attractive biocatalyst for the chemical conversion of bilirubin.

TABLE I

Calculated v'm/Km values from initial reaction rates for fixed hemoglobin and varied bilirubin concentrations.

| [BH2]o (mg/l) | V'm/Km (min$^{-1}$) | SYSTEM |
|---|---|---|
| 32.15 | 0.5111 | Free hemoglobin |
| 25.72 | 0.641 | " |
| 19.29 | 0.776 | " |
| 12.86 | 1.470 | " |
| 6.40 | 2.160 | " |
| 12.45 | 0.518 | Microcapsules |
| 7.47 | 0.578 | " |
| 4.99 | 0.842 | " |
| 2.50 | 1.926 | " |

TABLE II

Calculated Vm/Km values from initial reaction rates for fixed bilirubin concentrations and varied hemoglobin.

| HEMOGLOBIN (mg/l) | Vm/Km (min$^{-1}$) | SYSTEM |
|---|---|---|
| 3.22 | 0.111 | Free hemoglobin |
| 6.43 | 0.194 | " |
| 12.8 | 0.297 | " |
| 31.7 | 0.780 | " |
| 62.5 | 1.51 | " |
| 121.0 | 3.45 | " |
| 15.6 | 0.415 | Microcapsules |
| 20.4 | 0.554 | " |
| 32.0 | 0.797 | " |
| 40.4 | 1.01 | " |

TABLE III

Michaelis constants for bilirubin with either hemoglobin or bilirubin oxidase as catalyst.

| SYSTEM | Km (um) | Vmax (uM/Min.) |
|---|---|---|
| Free hemoglobin | 16.4 | 31.6 |
| Microcapsules | 10.1 | 15.8 |
| Bilirubin oxidase | 50.0 | — |
| Bilirubin oxidase | 40.0 | 0.44 |

Thus, based on equation 4 and on the values of Km and Vmax presented in Table III, it takes 19 minutes to reduce bilirubin from a severe jaundice level of 200 mg/l to an average normal value of 5 mg/l when hemoglobin is immobilized in collodion microcapsules. The amount of mirocapsulated hemoglobin required is only 23.3 mg for 1 liter of bilirubin solution. Similarly, the use of free hemoglobin requires 8.7 minutes. It will be understood by those skilled in the art that these times may be different for different reactor designs and mixing methods employed.

What is claimed is:

1. A process for oxidizing bilirubin which comprises reacting a solution containing bilirubin with immobilized hemoglobin in the presence of an oxidizing agent.

2. The process of claim 1 wherein the oxidizing agent is hydrogen peroxide.

3. The process of claim 2 wherein the concentration of hydrogen peroxide ranges between 1.0 to 100.0% weight of bilirubin.

4. The process of claim 1, wherein the oxidizing agent is glucose oxidase in the presence of glucose.

5. The process of claim 4, wherein hemoglobin and glucose oxidase are co-immobilized.

6. The process of claim 4, wherein the concentration of glucose oxidase ranges between 1.0 and 30% weight of bilirubin.

7. The process of claim 1, wherein hemoglobin is immobilized by microencapsulation, covalent linkage to a suitable carrier, entrapment or crosslinkage.

8. The process of claim 7, wherein hemoglobin and glucose oxidase are co-immobilized by microencapsulation, entrapment covalent linkage to a suitable carrier or crosslinkage.

9. The process of claim 1 wherein the concentration of hemoglobin ranges from 1.0 to 50% weight of bilirubin.

10. A process for oxidizing bilirubin which comprises reacting a solution containing bilirubin with hemoglobin having been previously immobilized in semipermeable microcapsules in the presence of hydrogen peroxide.

11. A process according to claim 10 where the hemoglobin is immobilized to a carrier by covalent linkage.

12. A process according to claim 10 where the hemoglobin is immobilized by intermolecular cross-linkage.

13. A process for oxidizing bilirubin which comprises reacting a solution containing bilirubin in the presence of glucose oxidase and hemoglobin, both hemoglobin and glucose oxidase having been previously co-immobilized in semipermeable microcapsules.

14. A process according to claim 13 where the hemoglobin and glucose oxidase are co-immobilized by intermolecular cross-linkage.

* * * * *